United States Patent [19]

Boucher et al.

[11] Patent Number: 4,570,027
[45] Date of Patent: Feb. 11, 1986

[54] ALKYLATION OF AROMATIC MOLECULES USING A SILICA-ALUMINA CATALYST DERIVED FROM ZEOLITE

[75] Inventors: Heather A. Boucher, Sarnia, Canada; Ian A. Cody, Baton Rouge, La.

[73] Assignee: Exxon Research and Engineering Co., Florham Park, N.J.

[21] Appl. No.: 603,033

[22] Filed: Apr. 27, 1984

[51] Int. Cl.$^4$ .................. C07C 2/64; C07C 15/107
[52] U.S. Cl. .................. 585/455; 585/467; 585/468
[58] Field of Search .................. 585/455, 467, 468

[56] References Cited

U.S. PATENT DOCUMENTS

| | | | |
|---|---|---|---|
| 2,329,858 | 9/1943 | Schmerling | 260/671 |
| 2,519,099 | 8/1950 | Bailey et al. | 260/671 |
| 2,526,907 | 10/1950 | Schmerling | 252/453 |
| 2,542,190 | 2/1951 | Gorin | 260/671 |
| 2,818,392 | 12/1957 | Appell | 252/435 |
| 2,852,576 | 9/1958 | Fotis et al. | 260/671 |
| 2,930,819 | 3/1960 | Aies | 260/671 |
| 2,930,820 | 3/1960 | Aries | 260/671 |
| 2,939,890 | 6/1960 | Herbert et al. | 260/671 |
| 2,972,642 | 2/1961 | Pfefferle | 260/671 |
| 3,092,981 | 6/1963 | Begeman et al. | 62/468 |
| 3,642,634 | 2/1972 | Olmed | 252/59 |
| 3,725,243 | 4/1973 | Hess et al. | 208/59 |
| 3,812,036 | 5/1974 | Romnine | 252/59 |
| 3,945,943 | 3/1976 | Ward | 252/455 |
| 4,094,922 | 6/1978 | Bartek et al. | 260/671 |
| 4,148,834 | 4/1979 | Kennedy et al. | 585/449 |
| 4,275,256 | 1/1981 | Chu et al. | 585/467 |
| 4,283,306 | 8/1981 | Herkes | 252/432 |
| 4,387,259 | 6/1983 | Barile | 585/467 |
| 4,387,260 | 6/1983 | Watson et al. | 585/467 |

FOREIGN PATENT DOCUMENTS

| | | |
|---|---|---|
| 0021600 | 1/1981 | European Pat. Off. . |
| 0029333 | 5/1981 | European Pat. Off. . |
| 0030084 | 10/1981 | European Pat. Off. . |
| 0064046 | 11/1982 | European Pat. Off. . |
| 896043 | 11/1953 | Fed. Rep. of Germany . |
| 1128239 | 8/1956 | France . |
| 813214 | 5/1959 | United Kingdom . |
| 1254656 | 11/1971 | United Kingdom . |
| 1414700 | 11/1975 | United Kingdom . |
| 2078776A | 1/1982 | United Kingdom . |
| 21149998A | 9/1983 | United Kingdom . |
| 2114999A | 9/1983 | United Kingdom . |

OTHER PUBLICATIONS

"Alkylated Aromatic Hydrocarbons as Components of Lubricating Oils", Volchinskaya, et al; Tr. Uses. Nauch, Isled Inst. Pererol Nefte No. 12, 155–162 (1970).
"Service Properties of Fuels and Oils–Lubricants Based on Dialkylbenzene" Kinau, et al., Khimya i. Tekhnologiya Topliv i Masil #5 pp. 35–38 (1971).
CA 22 3606(b), Alkylated Aromatic Hydrocarbons (Japan 162258).
CA 53, 9104, "Alkylation of Benzene by Propylene in Vapor Phase in Contact with Zinc Chloride Deposited on Solid Supports", Kuchkarev.

Primary Examiner—Curtis R. Davis
Attorney, Agent, or Firm—Joseph J. Allocca

[57] ABSTRACT

Aromatic molecules are alkylated using a silica-alumina catalyst derived from zeolite. The silica-alumina catalyst is a partially collapsed zeolite, i.e., a material of reduced crystallinity. The alkylation process which employs this material of reduced crystallinity is characterized by a high level of selectivity for the production of monoalkylated product.

17 Claims, 2 Drawing Figures

ALKYLATION OF AROMATIC MOLECULES USING A SILICA-ALUMINA CATALYST DERIVED FROM ZEOLITE

DESCRIPTION OF THE INVENTION

A process is described for the alkylation of aromatic molecules by use of a low crystallinity, partially collapsed zeolite catalyst. The process is marked by a high level of selectivity for the monoalkylation of the aromatic substrate. Selectivity for monoalkylation on the order of 96% is achieved.

BACKGROUND

Figure 1:
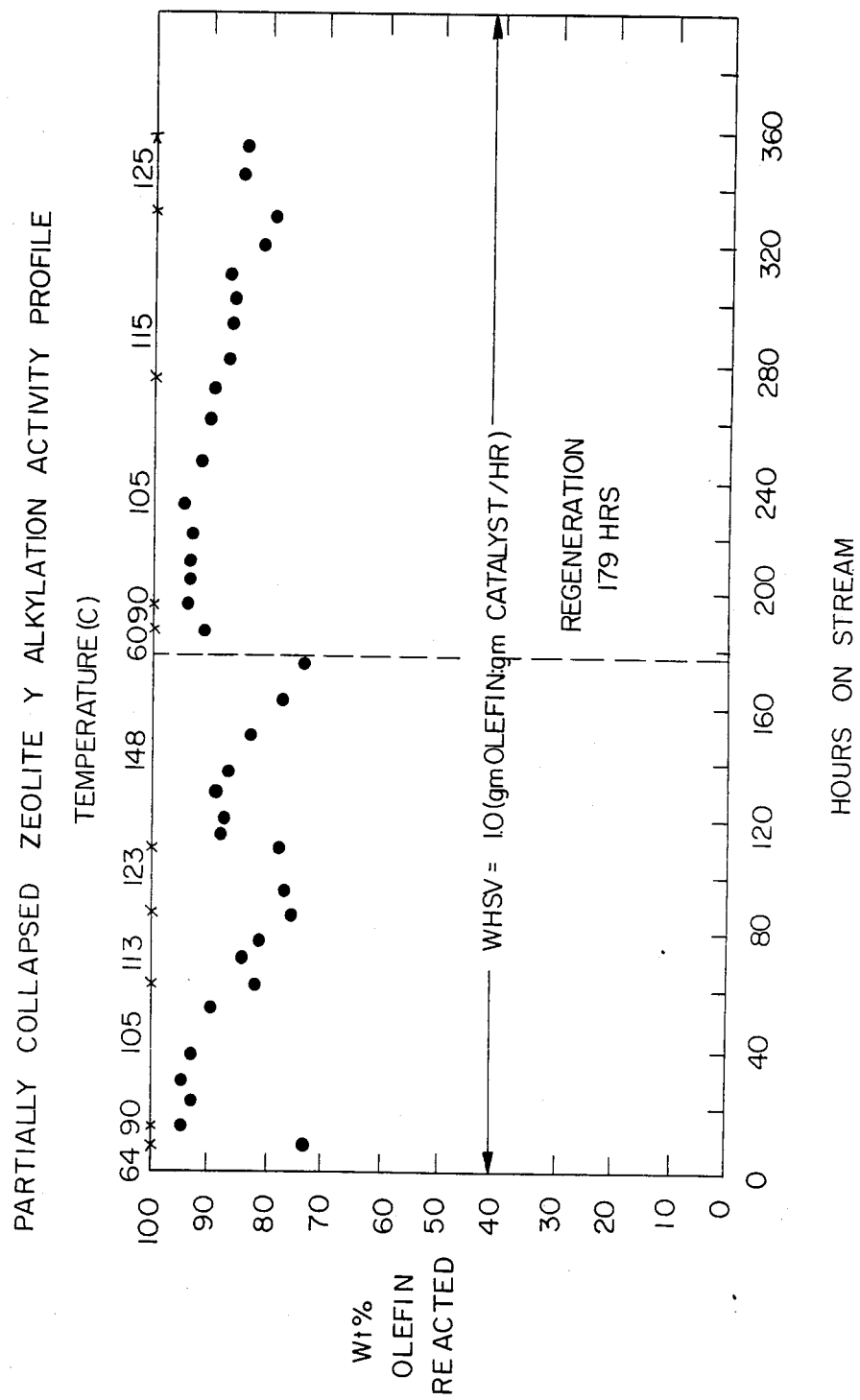
FIG. 1 presents the % n-hexadecene conversion as a function of time and temperature.

Light mononuclear aromatic molecules such as benzene, toluene and xylenes can be alkylated with alkylating agents such as olefins using acidic Friedel-Crafts catalysts or heterogeneous acidic silica-alumina catalysts. Generally, it is difficult to control the product distribution obtained from these reactions, and one normally obtains an appreciable amount of di-alkylation. As the products of mono-alkylation are usually the most valuable, the alkylation reaction is generally carried out using an excess of the aromatic component, in order to suppress di-alkylation. In spite of the use of rather large molar ratios of aromatic to olefin (for example, 3:1 to 8:1), some di-alkylation invariably occurs. Economic considerations determine the amount of excess aromatic in the feed, and the amount of di-alkylation which can be tolerated.

In recent years, acidic zeolites have been used to catalyse the alkylation reaction. These catalysts, however, are not very specific for mono-alkylation.

For example, U.S. Pat. No. 4,301,316 teaches the use of crystalline zeolite catalysts such as ZSM-20, mazzite, ZSM-38 and zeolite beta as aromatic alkylation catalysts. However, using a benzene:olefin mole ratio of 4:1, and various catalysts, the selectivity for mono-alkylation claimed in this patent varies only from 33 weight percent to 73 weight percent, and these selectivities occur at less than complete olefin conversion (maximum reported percentage of olefin conversion 94%). It is expected that as the olefin conversion is increased, the selectivity for monoalkylation will decrease. U.S. Pat. No. 4,301,417 teaches the use of crystalline zeolite catalysts characterized by channels having openings with major dimension of 6 to 7A. Such zeolites include ZSM-12, offretite, mordenite, etc. At an aromatic:olefin ratio of 4:1, selectivity for mono-alkylation is claimed to vary only from 53 weight percent (Example 1) to 80 weight percent (Example 8), using the different catalysts included in the patent. One example, using HZSM-12 (Example 7 of the patent), describes the alkylation of benzene with 1-dodecene at a benzene:1-dodecene ratio of 4:1. Selectivity for mono-alkylation was only 63 weight percent at 54 weight percent olefin conversion. The use of higher molar ratios of aromatics to olefin did not give rise to appreciably higher selectivities for mono-alkylation. Example 5 of the patent describes the alkylation of benzene with 1-octene at a molar ratio of 8:1 using HZSM-12 catalyst (steamed). Selectivity for mono-alkylation was only 83 weight percent at 88 weight percent olefin conversion.

The alkylation of aromatics with olefins for the production of alkylbenzene detergent alkylates is carried out industrially using the UOP hydrofluoric acid catalysed process. UOP claims (see "Linear Internal Olefins—A Commercial Intermediate for Detergents and Plastics, R. C. Berg, R. A. Persak, G. R. Winter, UOP Process Div., 1975 UOP Process Division, Technology Conference, Sept.–Nov. 1975) their product contains 91.2 weight percent monoalkylaromatics and 8.8 weight percent di-alkylaromatics. The benzene:olefin ratio used in the reaction is not specified, but probably lay in the range 6 to 9.

The prior art does not specifically address the preparation of monoalkylaromatics with high selectivity, despite the fact that the production of di-alkylaromatic by-products is a large debit in the detergent industry.

THE PRESENT INVENTION

The present process alkylates mono- and polynuclear aromatic molecules which are generally selected from benzene, toluene, o-, m-, and p-xylene, ethylbenzene, n- or iso-propyl benzene, n, iso- and tert-butyl benzene, tetralin, alkyltetralin, naphthalene, alkylnaphthalenes and mixtures thereof, preferably benzene toluene, the xylenes and ethylbenzene, most preferably ethyl benzene. The alkylating agent includes any aliphatic or aromatic organic compound which is capable of reacting with an aromatic compound. Useful alkylating agents include, for example, alkyl halides, olefins and alcohols. Olefins having from 3 to 20 carbons are typically employed as the alkylating agent, although any class of compounds capable of generating olefins under alkylation conditions can also be employed, however, long chain linear olefins (both internal random and alpha) containing from 10 to 20 carbons are the preferred alkylating agent. The monoalkylated aromatic product typically possesses a total of from 16–28 carbons, preferably from 18–26 carbons, more preferably 20–26 carbons. The long chain monoalkylation products of the present process are useful in the detergent industry. Certain of the monoalkylated alkyl benzenes (i.e. dialkyl benzenes containing one short (2–4 carbon) and one long (14–18 carbon) alkyl groups and containing a total of 23–28 carbons, preferably 24–26 carbons) have been found to be useful as synthetic lubricating oil basestocks and basestock additives, as disclosed and claimed in copending application U.S. Ser. No. 603,032, filed even date herewith.

The alkylation product may be purified if necessary and/or recovered from the starting materials or coproduced by products by standard separation techniques. For example, the presence of unsaturated olefinic dimer in the alkylation product may be undesirable in applications where good oxidation stability is required. In this case, hydrogenation, either with an olefin-specific hydrogenation catalyst or with a hydrogenation catalyst which will saturate the olefin dimer and convert the alkylaromatics to naphthenes, may be desirable. Alternatively, purification may be carried out by physical separation techniques such as distillation or selective permeation through a permselective membrane such as an asymmetric reverse osmosis polyimide membrane. Such a procedure for separating the alkylation product from the starting material and byproducts and the simultaneous separation of the alkylate product into its isomers using membranes is described and claimed in copending application U.S. Ser. No. 603,028, filed even date herewith.

The present alkylation process, however, is marked by a very high degree of mono-alkylation (very little byproduct is produced) such that separation processes are of little importance. Recovery of the mono-alkylate product from starting material is efficiently handled by distillation or simple stripping. The mono-alkylated alkyl benzene products which are useful as specialty and lube oils (in accordance with U.S. Ser. No. 603,032) can be used as produced, that is, there is no need to separate the dialkylbenzene product into its various isomers or to separate the dialkyl benzene from the bulk reaction product mixture, other than to effect solvent recovery which can be by distillation and diolefin removal which can be handled by hydrogenation.

In the practice of the present alkylation process using the acidic low crystallinity partially collapsed zeolite the alkylation conditions employed are as follows: a temperature of between about 50° to 200° C., preferably about 60°–150° C., more preferably about 70° to 140° C.; at a pressure of about 0 to 2,000 psig, preferably about 0–500 psig, more preferably about 0–300 psig, most preferably about 0–200 psig at a space velocity (WHSV gm olefin:gm catalyst/hr) of about 0.1 to 10 hr$^{-1}$, preferably about 0.5 to 4 hr$^{-1}$, most preferably about 0.8 to 2 hr$^{-1}$. The reaction can be run neat or in the presence of a dry gas atmosphere, such as nitrogen or hydrogen. The molar ratio of aromatic to alkylating agent (preferably olefin) starting material is about 1:1 to 10:1, preferably about 2:1 to 8:1, most preferably about 3:1 to 5:1.

The process of the present invention can be practiced in either a batch or continuous mode, the continuous mode being preferred.

In practicing the present process a metal free, acidic low crystallinity partially collapsed zeolite is employed as the catalyst. The procedure employed to produce the low crystallinity, partially collapsed zeolite generally is described in copending application U.S. Ser. No. 416,092, filed Sept. 8, 1982, now U.S. Pat. No. 4,515,681. In general the procedure involves deeply exchanging the cation sites of the zeolite, preferably a wide pore zeolite such as Zeolite Y or Zeolite X, most preferably Zeolite Y, with ions which can be thermally decomposed into hydroxyl groups, such as the organic and inorganic ammonium salts, such as ammonium halides, e.g., chlorides, bromides, ammonium carbonates, ammonium thiocyanates, ammonium hydroxide, ammonium molybdate, ammonium dithionate, ammoniumnitrate, ammonium sulfate, ammonium formate, ammonium lactate, ammonium tartrate, and the like, hydrocarbon and organic amines, such as the class of organic nitrogen bases, including pyridine, guanidine and quinoline salts, polyhydrocarbyl ammonium salts, such as the tetraalkyl and tetraaryl salts, e.g., tetramethylammonium hydroxide and tetraethylammonium hydroxide, preferably NH$_4$+ ions, drying the exchanged zeolite, then calcining the exchanged zeolite in a relatively dry atmosphere, preferably dry air, so as to reduce the crystallinity of the material as compared with the zeolite starting material. The degree of cation exchange is generally to a level of greater than about 50%, with exchanges to a level of greater than 70% being preferred. The exchanged zeolite is dried so as to preferably contain no more than an equilibrium amount of moisture. Drying may take the form of permitting the sample to evaporate most of its moisture off into the atmosphere, but preferably deliberate drying is practiced, for example, heating to about 120° C. for an hour or more depending on sample size, or pumping off the moisture by application of a vacuum, etc. The calcination is conducted in a thin bed at a temperature of at least about 300° C. (generally about 300° to 600° C.) in a relatively dry atmosphere, e.g., an atmosphere which generally contains less than about 1 psi, preferably less than about 0.2 psi, water vapor partial pressure at the conditions used. This calcination may be conducted in air, hydrogen or any gas which is inert, i.e., does not interact with the zeolite, preferably dry air. The calcined material may then be further treated by roasting in an inert-non-reactive or reducing atmosphere containing no more than trace amounts of moisture, or in a vacuum, at from 400° to 900° C.

The crystalline zeolite starting material is subjected to the above recited procedure so as to produce a low crystallinity partially collapsed zeolite product marked by having about 30–80% retained crystallinity as measured by XRD. Crystallinity losses of greater than about 70% are not desirable in the catalyst used in the present invention since such a material has been found to be not as selective or as active for the monoalkylation process described herein. Crystallinity loss can be controlled by adjusting either or both of the amount of moisture present in the environment during the calcination step (the greater the moisture content the lower the loss of crystallinity) and/or the thickness of the bed of the cation exchanged material in the calcination oven (the thicker the bed of cation exchanged material, the lower the loss of crystallinity at a given calcination temperature). The low crystallinity, partially collapsed zeolite which is preferred for use in the present invention therefore has about 30–80% retained crystallinity as determined by x-ray diffraction (XRD). The percentage of retained crystallinity in a low crystallinity, partially collapsed zeolite sample is obtained by averaging the heights of five major peaks in its XRD pattern and comparing this value to the average of the heights of these five peaks in the XRD pattern of the parent sodium zeolite. The five (major) peaks which are used in the calculation are those which occur at $\theta°$ values of 15.5, 20.2, 23.5, 26.9 and 31.3.

Monoalkylation is usually the most desired reaction when carrying out an alkylation reaction. Because of the ability of these acidic, low crystallinity, partially collapsed zeolite catalysts to maximize the yield of the product of monoalkylation, it is possible that the alkylation reaction can be carried out using a lower molar ratio of aromatic to olefin in the feed stream. This would improve the economics of the process, as any excess aromatic used in the reaction must be removed from the products. The selectivity for monoalkylation observed using these catalysts is very high, generally being about 90% or more, at times about 96% or more, approaching 99+%. High selectivity has not been reported with purely zeolitic catalysts or with homogeneous catalysts such as hydrofluoric acid. In those cases, where a broader product distribution is obtained, fairly complicated separation schemes such as the membrane separation schemes identified above are required, and in the case of typical Friedel-Crafts catalysts (using, e.g., AlCl$_3$ or HF) purification procedures are also required if the product is to be acceptable for use as a synthetic lube oil basestock or basestock additive.

It has been found that samples of Zeolite Y which possess reduced crystallinity, as mentioned above, are active catalysts for the alkylation of aromatic hydrocarbons, such as benzene, toluene, ethylbenzene, tetralin and naphthalene with olefins. The activity and selectivity exhibited by the catalyst depends strongly on the degree of crystallinity retained by the catalyst. In particular, Zeolite Y which has been deeply exchanged with $NH_4^+$ ions, calcined (preferably in air) at a temperature between about 350° C. and 550° C., in a thin bed configuration and then conditioned in a hydrogen atmosphere up to a temperature of 450° C., exhibits very high selectivity for monoalkylation of light aromatic molecules with linear olefins. XRD analyses showed that the material possessed a percentage of crystallinity greater than 30%, but less than 100%. Materials possessing a percentage of crystallinity less than about 30% are useable but exhibit inferior selectivity and activity and are not preferred for that reason.

Consequently, the catalyst preparation parameters employed are selected from the ranges recited above, but chosen employing the guidelines respecting mixture content, temperature and bed thickness previously recited so as to provide a material possessing about 50% retained crystallinity.

The present invention will be better understood by reference to the following examples which are presented solely by way of example and not limitation.

EXAMPLE A—PRODUCTION OF PARTIALLY COLLAPSED ZEOLITE Y

375 CC of Zeolite Y obtained from Union Carbide (identified as EC-66) and having an as received anhydrous composition of

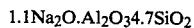

1.1Na$_2$O.Al$_2$O$_3$4.7SiO$_2$ was refluxed in a 10:1 volume excess of 2N ammonium nitrate for 2 hours. The hot mixture was filtered, and the refluxing exchange procedure was repeated, this time for 19 hours. The solid was collected by filtration, washed well with deionized water, dried at 120° C. and equilibrated with lab air. The dry powder was pressed at 1 ton pressure into a solid cake which was broken into small pieces, and sized using 7/14 mesh screens. 100 ccs (42.1 g) of catalyst was spread as thinly as possible on an 8"×10" screen, placed in an oven at 450° C. through which flowed lab air of ambient humidity at 7.0 cuft/hr, and held at 450° C. for 1 hour. The catalyst was allowed to cool to room temperature in the open for 4 hours.

At the beginning of the run, the catalyst was placed in the reactor. The reactor was pressure tested cold with N$_2$ and H$_2$ at 270 psig, then heated to 100° C. over a 2 hour period at a hydrogen flow rate of 3.0 cuft/hr and held at 100° C. for 1 further hour. The reactor was then heated to 450° C. at a rate of 2° C./minute with H$_2$ at 200 psig, and held at 450° C. for 1 hour at an H$_2$ flow rate of 3.0 cuft/hr. The reactor was then cooled to 60° C. under a flow of H$_2$ of 3.0 cuft/hr.

Alkylation

Alkylation of ethylbenzene with a α-n-hexadecene was carried out in pilot plant operating upflow. Standard conditions were 180 psig (H$_2$), 1.5 cuft/hr H$_2$, with a feed consisting of a 5:1 molar ratio of ethylbenzene:α-n-hexadecene. Temperature was the main variable, this being adjusted as required to obtain conversions of 80% or more. Initial temperature in the runs was 65° C. Temperature was then raised stepwise to the desired operating range of 105° C. to 150° C. Temperatures above 150° C. are avoided as undesirable olefin skeletal rearrangements occur. Generally, a WHSV of 1.0 hr$^{-1}$ (g. olefin: g. catalyst/hr) was used.

FIG. 1 illustrates the percent α-n-hexadecene conversion and the reactor temperature at various times during the alkylation run using the partially collapsed Zeolite Y. The reactor was maintained at a specific temperature until conversion of α-n-hexadecene to alkylation product began to decrease, then the temperature was increased in 10° to 20° C. increments. The first run was continued for a total of 179 hours, at which time the extent of conversion was undesirably low and decreasing at 148° C. Regeneration was accomplished by burning using 2.4% oxygen in nitrogen at 450° C. for 48 hours. Analysis of the product gases during this time indicated that most of the burn off was accomplished in the first 24 hours.

The first run using this catalyst (that is, 0 to 179 hours on stream) indicated that, although catalyst activity was high, the onset of deactivation was fairly rapid and frequent temperature increases were required to maintain olefin conversion. However, catalyst life maintenance was considerably improved after regeneration (that is, 179-359 hours on stream). In this case, olefin conversion remained at 90%+ at 105° C. for 80 hours, in contrast to 44 hours under similar conditions in the first run.

Throughout the entire 359 hours on stream, this catalyst was selective for the production of the mono-alkylation product, ethylhexadecylbenzene. Selectivity for monoalkylation was at all times greater than 99%, and usually >99.5% as determined by gas chromatographic analysis of the product stream (see Table 1).

Figure 2:
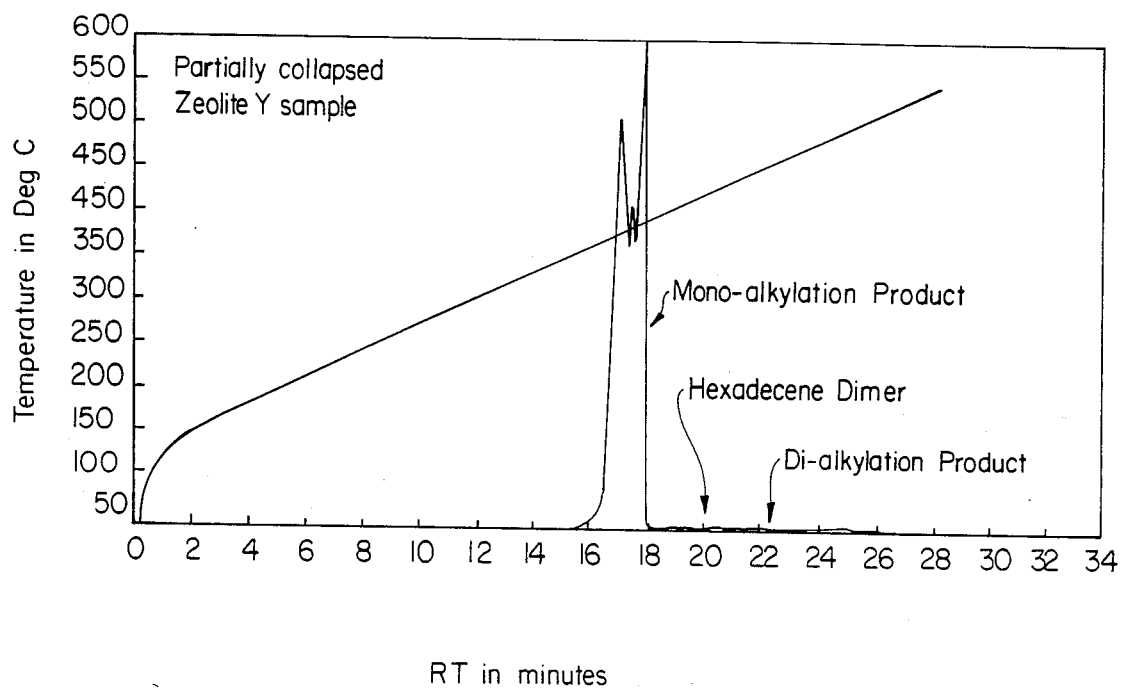
FIG. 2 represents a gas chromatographic trace of the composition of a stripped pilot plant bulk reaction product.

Due to the high selectivity of the partially collapsed Zeolite Y catalyst for monoalkylation, very little α-n-hexadecene dimer is present in the product stream. As this dimer, an olefin, is the main source of oxidation instability in the alkylation product, its near absence may mean that the bulk product need not be hydrogenated. To check this, samples 238-246 (hour) inclusive were combined, and stripped to remove unreacted ethylbenzene and hexadecene. The gas chromatographic trace of this bulk reaction product is shown in FIG. 2. This material was subjected to a modified D2440 oxidation test (see Table 2). This test evaluates the oxidation stability of the oil, and involves bubbling oxygen (1 l/hr) through a 50 g sample of the heated oil (110° C.) which contains oxidation inhibitor (0.06 wt% DBPC) and an oxidation catalyst (copper wire). The effluent oxygen is passed through water, which absorbs volatile acids produced on degradation of the oil. The extent of oxidative degradation of the oil at any time is determined by monitoring the accumulated amount of acids absorbed in the water. Completion of the test is determined to be when the total accumulated volatile acidity is equivalent to 5 mg KOH/g oil. The result, a lifetime of 353 hours, indicates that the sample has remarkable oxidation stability, considering that no attempt was made to remove hexadecene dimer nor was any other purification procedure employed. Such behavior indicates that the processing scheme using this alkylation catalyst may simply consist of alkylation followed by simple stripping to remove unreacted starting materials.

The physical properties of the material evaluated in the above oxidation test are given in Table 3. These properties of low viscosity, high viscosity index and low pour point, indicate that this material would be an excellent low viscosity blending stock, particularly in the formulation of light multi-grade oils such as a 5W30 grade.

The crystallinity of the spent alkylation catalyst was determined to be 44%.

TABLE 1

PRODUCT DISTRIBUTION OBTAINED IN THE ALKYLATION REACTIONS

| | Low Crystallinity H, sodium Zeolite Y | | |
|---|---|---|---|
| Catalyst Product | Monoalkylation Product | Dialkylation Product | Hexadecene Dimer |
| Sample Number | | | |
| Run 1-23 | 99.65% | 0.29% | 0.06% |
| -55 | 99.67% | 0.25% | 0.08% |
| -137 | 99.64% | 0.36% | |
| -246 | 99.26% | 0.68% | 0.06% |
| -310 | 99.78% | 0.22% | 0 |
| Run 1 - Samples 238-246 inclusive | 99.67% | 0.25% | 0.08% |

TABLE 2

OXIDATION STABILITY OF THE BULK ALKYLATION PRODUCTS (NOT HYDROGENATED)

| Catalyst | Low crystallinity H, sodium-Zeolite Y |
|---|---|
| Sample Numbers | 238-246 |
| D2440 Oxidation Test* hours to 5 mgKOH/g oil | 353 |

*110° C., 1l O₂/hr, copper wire catalyst, 0.06 wt. % DBPC

TABLE 3

PHYSICAL PROPERTIES OF BULK ALKYLATION PRODUCTS (NOT HYDROGENATED)

| Catalyst | Low crystallinity H, sodium-Zeolite Y |
|---|---|
| Sample Numbers | 238-246 |
| Viscosity, cSt, 40° C. | 10.48 |
| 100° C. | 2.76 |
| Viscosity Index | 104 |
| Pour Point, °C. | −45 |
| Volatility (LV % off, 375° C.) | 11 |

EXAMPLE B

Zeolite Y obtained from Union Carbide Corp., and having an "as received" anhydrous composition of 1.1Na$_2$O.Al$_2$O$_3$.4.7SiO$_2$ was twice refluxed in a 10:1 volume excess of 2N ammonium nitrate solution for 2 hours. The zeolite was washed free of NO$_3$, dried at 120° C. and allowed to equilibrate with laboratory air at room temperature. The catalyst was pelletized, sieved (7/14 mesh), then calcined in moist (laboratory) air at 450° C. for 1 hour. 22.89 g (50 cc) of the catalyst was loaded in a continuous flow reactor, and conditioned in pure dry hydrogen gas (50 psig, 3.0 cuft/hr) according to the following procedure.

1. temperature increased from ambient to 100° C. over a 2 hour period;
2. temperature held at 100° C. for 1 hour;
3. temperature increased from 100° C. to 450° C. at a rate of 2° C./min;
4. the temperature was reduced quickly from 450° C. to ambient.

A feed stream consisting of toluene and a α-n-hexadecene (molar ratio 5:1) was passed upflow over the catalyst at a total LHSV of 1.67 hr$^{-1}$, maintaining a pressure of 180 psig H$_2$ (gas flow rate 1.5 cuft/hr), at a temperature of 104° C. Gas chromatographic analysis of the product stream indicated a 94.5% conversion of α-n-hexadecene, with >98.5% selectivity to n-hexadecytoluene, the remainder being α-n-hexadecene dimer and di-n-hexadecyltoluene.

The crystallinity of a sample of the the spent alkylation catalyst was determined to be 70% by x-ray diffraction.

EXAMPLE C

The catalyst preparation procedure described in Example B was repeated except that the ammonium-exchanged Zeolite Y was dried at 120° C., air-equilibrated, pelletized and sieved, and then loaded directly into the reactor without calcination.

The catalyst was then conditioned in H$_2$ gas to 450° C., as described in Example B.

A feed stream consisting of toluene and α-n-hexadecene (5:1 molar ratio) was passed upflow over the catalyst under the conditions described in Example 1. Samples of the product stream produced at reactor temperatures of 105° C. were subjected to gas chromatographic analysis. Conversion of α-n-hexadecene was 67.9%, and selectivity to n-hexadecyltoluene was 71.8%. This lower selectivity and conversion shows the desirability of dry atmosphere calcining of the catalyst before use.

The crystallinity of a sample of the spent alkylation catalyst was determined to be 44% by x-ray diffraction.

EXAMPLE D

The catalyst preparation procedure described in Example B was repeated except that the ammonium-exchanged Zeolite Y was calcined at 600° C., instead of 450° C., for 1 hour. The catalyst was conditioned in H$_2$ gas to 450° C., as described.

A feed stream consisting of toluene and α-n-hexadecene (5:1 molar ratio) was passed upflow over the catalyst under the same conditions described in Example B. Samples of the product stream produced at 102° C. were subjected to gas chromatographic analysis. Conversion of α-n-hexadecene was 36.5%, and selectivity to n-hexadecyltoluene was 20.8%. The crystallinity of a sample of the spent alkylation catalyst was determined to be <10% by x-ray diffraction.

EXAMPLE E

A sample of Union Carbide Zeolite Nax was twice exchanged with ammonium nitrate solution as described in Example B, washed free of nitrate ion, dried at 120° C. and allowed to equilibrate with air at room temperature. The catalyst was pelletized, sieved (7/14 mesh), then calcined in breathing air at 450° C. for 1 hour. The catalyst was quickly loaded into a continuous flow reactor, and conditioned in pure dry hydrogen gas (50 psig, 3.0 cuft/hr) as described in Example B.

A feed stream consisting of mixed xylenes and α-n-hexadecene (molar ratio 5:1) was passed upflow at a WHSV (g olefin:g catalyst/hr) of 0.95 hr$^{-1}$, maintaining a pressure of 180 psig H$_2$ (gas flow rate 1.5 cuft/hr). The catalyst was active for alkylation even before the heat was applied. After 2 hours without external heating, gas chromatographic analysis of the product stream indicated 21% conversion of α-n-hexadecene, with 95.9% selectivity for mono-alkylation of the xylenes.

Catalyst activity decreased and the reaction was heated to 60° C. After a total of 6 catalyst hours, conversion of α-n-hexadecene (at 60° C.) was 4%, with 57% selectivity for mono-alkylation of the xylenes.

As catalyst activity was low and declining, the temperature was increased to 110° C. At 12 hours on stream, conversion of α-n-hexadecene was 15%, with selectivity for mono-alkylation of the xylenes being 79%. Due to the low (and continually) declining) activity of the catalyst, the run was terminated.

The crystallinity of the spent alkylation catalyst was determined to be 0% by x-ray diffraction.

EXAMPLE F

Zeolite Y catalyst was prepared and conditioned in dry $H_2$ gas as described in Example B, and used in a run to determine the effect of pressure on the alkylation reaction.

A feed stream consisting of toluene and α-n-hexadecene (5:1 molar ratio) was passed upflow over the catalyst at a total LHSV of 1.67 hr$^{-1}$, maintaining a pressure of 180 psig $N_2$, (gas flow rate 1.5 cuft/hr). The temperature was gradually increased from ambient, and was set at 100° C. after 29 hours on stream. Olefin conversion as determined by gas chromatographic analysis of spot samples was 97% at 35 hours on stream, and olefin selectivity for mono-alkylation was 98.6%. At this time, the pressure was decreased to 35 psig, which caused olefin conversion to rise to 99.2% and olefin selectivity for mono-alkylation to decrease to 97.6%. Olefin conversion remained constant until 58.5 hours on stream when the pressure was increased to 180 psig (still at 100° C.). This pressure increase caused an immediate decrease in the amount of olefin conversion to 90%, and the olefin selectivity for mono-alkylation to rise to 98.7%. The pressure was decreased to 35 psig at 81 hours on stream, which caused a rapid increase in the olefin conversion, to 96%. These results indicate that olefin conversion is enhanced when the reaction is carried out at low pressures rather than at high pressures. The crystallinity of the spent catalyst was determined to be 52%.

What is claimed is:

1. A method for producing alkylaromatic hydrocarbons comprising contacting an aromatic hydrocarbon with an alkylating agent in the presence of a low crystallinity, partially collapsed zeolite.

2. The method of claim 1 wherein the low crystallinity partially collapsed zeolite is a partially collapsed wide pore zeolite.

3. The method of claim 1 wherein the low crystallinity, partially collapsed zeolite possesses about 30 to 80% retained crystallinity as determined by XRD.

4. The method of claim 2 wherein the low crystallinity, partially collapsed wide pore zeolite possesses about 30 to 80% retained crystallinity as determined by XRD.

5. The method of claim 3 wherein the low crystallinity, partially collapsed zeolite possesses about 50% retained crystallinity as determined by XRD.

6. The method of claim 4 wherein the low crystallinity, partially collapsed wide pore zeolite possesses about 50% retained crystallinity as determined by XRD.

7. The method of claim 1, 2, 3, 4, 5 or 6 wherein the aromatic hydrocarbon is a mono or poly nuclear aromatic hydrocarbon.

8. The method of claim 7 wherein the aromatic hydrocarbon is selected from benzene, toluene, o-, m- and p-xylene, ethylbenzene, n- and iso-propyl benzene, n, iso- and tert-butylbenzene, tetralin, alkyltetralin, naphthalene and alkyl naphthalenes.

9. The method of claim 8 wherein the aromatic hydrocarbon is benzene, toluene, o-, m- or p-xylene or ethylbenzene.

10. The method of claim 9 wherein the aromatic hydrocarbon is benzene or ethylbenzene.

11. The method of claim 1, 2, 3, 4, 5 or 6 wherein the alkylating agent is a $C_3$ to $C_{20}$ olefin.

12. The method of claim 7 wherein the alkylating agent is a $C_3$ to $C_{20}$ olefin.

13. The method of claim 8 wherein the alkylating agent is a $C_3$ to $C_{20}$ olefin.

14. The method of claim 9 wherein the alkylating agent is a $C_{10}$ to $C_{20}$ olefin.

15. The method of claim 10 wherein the alkylating agent is a $C_{10}$ to $C_{20}$ olefin.

16. The method of claim 1, 2, 3, 4, 5 or 6 wherein the alkylating reaction is conducted at a temperature of between about 50° to 200° C., at a pressure of about 0 to 2000 psig, at a space velocity (WHSV gm olefin:gm catalyst/hr) of about 0.1 to 10 hr$^{-1}$ at a molar ratio of aromatic to alkylating agent starting material of about 1:1 to 10:1.

17. The method of claim 16 wherein the low crystallinity partially collapsed zeolite is a zeolite Y.

* * * * *